(12) United States Patent
Herbert et al.

(10) Patent No.: US 6,867,698 B2
(45) Date of Patent: Mar. 15, 2005

(54) SYSTEM AND METHOD FOR AUTOMATICALLY LOGGING ARTICLE USE AND AN ARTICLE ADAPTED FOR SUCH

(75) Inventors: David Russell Herbert, Rockingham (AU); Shane McIvor, Mid Canterbury (NZ)

(73) Assignee: Herbert McIvor Holdings Pty Ltd. (AU)

( * ) Notice: Subject to any disclaimer, the term of this patent is extended or adjusted under 35 U.S.C. 154(b) by 71 days.

(21) Appl. No.: 10/149,037

(22) PCT Filed: Dec. 8, 2000

(86) PCT No.: PCT/AU00/01534

§ 371 (c)(1),
(2), (4) Date: Oct. 3, 2002

(87) PCT Pub. No.: WO01/42991

PCT Pub. Date: Jun. 14, 2001

(65) Prior Publication Data

US 2003/0076220 A1 Apr. 24, 2003

(30) Foreign Application Priority Data

Dec. 8, 1999 (AU) .............................................. PQ4534

(51) Int. Cl.⁷ .............................................. G08B 23/00
(52) U.S. Cl. ................. 340/573.1; 340/571; 340/572.1; 340/572.4; 340/572.5; 340/5.8; 340/5.92; 340/825.36
(58) Field of Search .......................... 340/573.1, 572.1, 340/572.4, 572.5, 5.8, 5.92, 825.36, 571

(56) References Cited

U.S. PATENT DOCUMENTS

| | | | |
|---|---|---|---|
| 4,881,061 A | * 11/1989 | Chambers ................. | 340/572.1 |
| 4,919,950 A | 4/1990 | Mak | |
| 5,267,889 A | 12/1993 | Sjoberg | |
| 5,334,084 A | 8/1994 | O'Brien et al. | |
| 5,478,990 A | 12/1995 | Montanari et al. | |
| 5,609,512 A | 3/1997 | Holmes et al. | |
| 5,745,036 A | * 4/1998 | Clare ....................... | 340/572.1 |
| 5,902,177 A | 5/1999 | Tessier et al. | |
| 5,964,565 A | 10/1999 | Lawler, Jr. et al. | |
| 5,973,606 A | 10/1999 | Maitin et al. | |
| 6,025,780 A | * 2/2000 | Bowers et al. ........... | 340/572.3 |
| 6,195,006 B1 | * 2/2001 | Bowers et al. ........... | 340/572.1 |

FOREIGN PATENT DOCUMENTS

| | | |
|---|---|---|
| WO | WO98/36645 | 8/1998 |
| WO | WO00/45331 | 8/2000 |

* cited by examiner

*Primary Examiner*—Daniel Wu
*Assistant Examiner*—Tai T. Nguyen
(74) *Attorney, Agent, or Firm*—Marger Johnson & McCollom, PC

(57) ABSTRACT

A system and method for automatically logging data pertaining to a particular use of an article, in particular the use of a boning or carving knife in a meat works. The knife having identifying means incorporated therein to identify a unique code for the particular knife. A reader is provided at a reading station to automatically read the unique code of a knife passed adjacent the reader. Data logging means is associated with the reader to log the unique code and the time at which the unique code was read by the reader. The data logging means is associated with one or more readers and reading stations located in an area where the knife is to be used. The area has reading stations associated with one or more treatment or storage locations for the knife at which a reader is disposed in a manner so that any passage of a knife from or to the treatment or storage location requires the article to be passed adjacent to the reader to enable the unique code of the knife to be automatically read by the reader. One of the treatment or storage locations includes a steriliser for sanitising the knife at prescribed intervals. An alarm and reminder alarm may also be associated with the system to alert an operator of the knife when it is due for sanitising or if it hasn't been sanitised properly. The application of the system to gloves and other articles is also described.

38 Claims, 2 Drawing Sheets

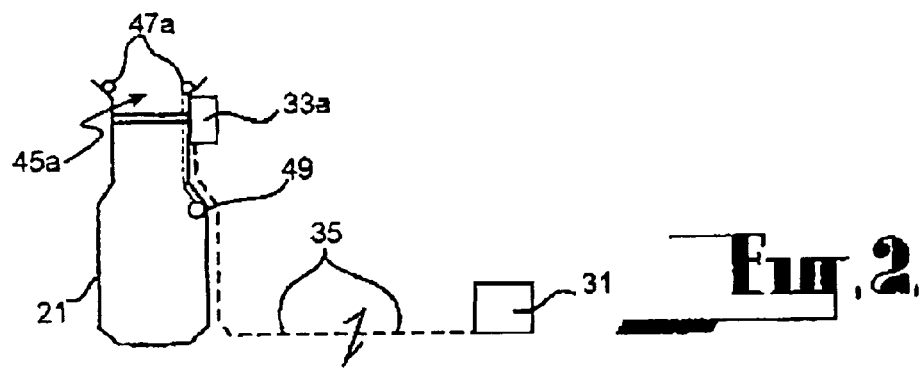
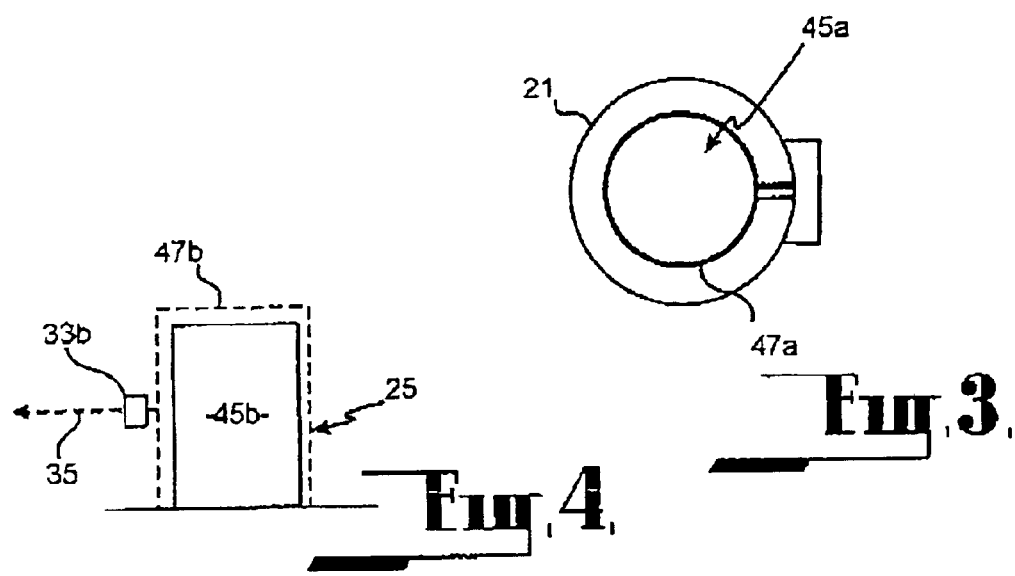
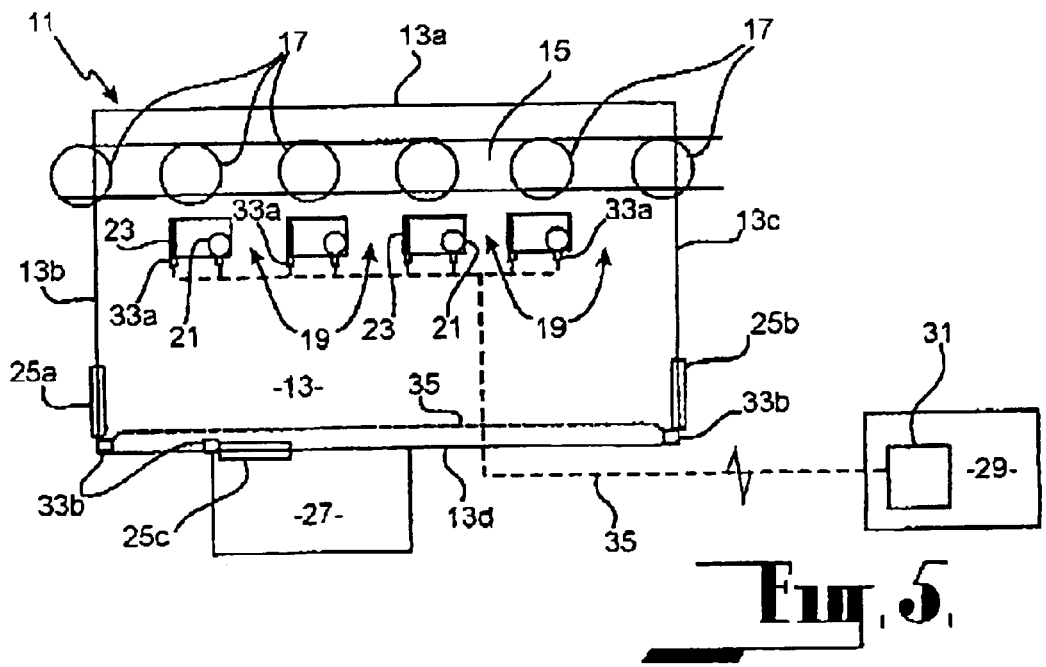

SYSTEM AND METHOD FOR AUTOMATICALLY LOGGING ARTICLE USE AND AN ARTICLE ADAPTED FOR SUCH

FIELD OF THE INVENTION

This invention relates to a system and method for automatically logging of data pertaining to a particular use of an article to enable monitoring and control of the use of that article in the light of the data so logged having regard to hygiene considerations, as appropriate. The invention has particular utility with the use of knives in the meat, fish and food handling industries generally.

Throughout the specification, unless the context requires otherwise, the word "comprise" or variations such as "comprises" or "comprising", will be understood to imply the inclusion of a stated integer or group of integers but not the exclusion of any other integer or group of integers.

BACKGROUND ART

In the meat and fish handling industry, knives are used extensively for skinning and boning carcasses of animals, and generally cutting different types of meat and fish, in large quantities for human consumption. Consequently, hygiene considerations are paramount in meat and fish handling places such as abattoirs, meatworks, butchers, fish production and processing plants and fishmongers, given the increased awareness of how disease can be easily spread from contaminated product at these places to the consumer.

For example, health regulations in Australia and New Zealand for abattoirs, require that the knife of a knife handler be thoroughly sterilised in a steriliser at least once every hour to ensure that micro-organisms picked up from the carcasses in the batch handled during that hour, are not passed on to the next batch, and so on. It is proposed that these time periods be decreased, with there even being talk that soon it will be necessary to sterilise a knife after use on just one carcass, before it is allowed to be used on another carcass.

In Europe, the British government is auditing and publishing results, which rank the nation's 1300 abattoirs in descending order according to the abattoir's hygiene performance. Other governments are following this lead.

Whilst these rules and regulations go some way to improving hygiene standards, there is still a need to police and enforce them to ensure that they are observed and complied with. Such policing and enforcement in the meat and fish handling industry is a major problem due to the large numbers of carcasses and fish that are worked on by a knife handler during a shift to meet quota, and the difficulty and cost in continuously watching over the actions of the knife handler. Indeed the knife handler is oftentimes too preoccupied with his or her work to be conscious of regular sterilising times and consequently this is often overlooked, quite unintentionally.

Another problem with the use of knives in such environments is that there is a tendency for them to become displaced, for example, from one area working on skinning of the carcasses, to another area working on gutting, to a further area still working on final cuts of meat, to another area in which the main knife grinding room is located. These different areas may have different hygiene standards, and movement of unsterilised knives from one area to another may be strictly forbidden for the reason that it may pass on dangerous microbes collected in one area to another area.

DISCLOSURE OF THE INVENTION

It is an object of the present invention to provide for the automatic logging of data pertaining to the particular use of an article that can allow for monitoring and controlling the use of that article in the light of the data so logged having regard to hygiene considerations.

In accordance with one aspect of the present invention, there is provided a system for automatically logging data pertaining to a particular use of an article, comprising:

an article having an identifier incorporated therein to identify a unique code for said article;

a first reader of said identifier disposed at a reading station to automatically read said unique code in response to the article being passed adjacent said first reader;

a data logger associated with said first reader to log said unique code and a time at which said unique code was read by the first reader;

said data logger being associated with one or more readers and reading stations located in an area where the article is to be used; and said area having reading stations associated with one or more treatment or storage locations for the article; and a second reader being disposed at each treatment or storage location in a manner so that any passage of a said article from or to a said treatment or storage location requires the article to be passed adjacent said second reader at said reading station to enable said unique code in respect thereof to be automatically read by said second reader;

wherein one of said treatment or storage locations includes a sanitiser to sanitise said article at prescribed intervals and said second reader is prompted to read and log said unique code and said time in connection with articles passing to and from said sanitiser for sanitising thereof.

Preferably, said area has reading stations associated with one or more prescribed or controlled accessways thereto and therefrom, and a first reader is disposed at each accessway, such that any passage of a said article from or to the area will require the article to be passed adjacent a first reader at a said reading station so that said unique code in respect thereof will be automatically read by said first reader.

Preferably, the identifier comprises a transponder including a wireless communicator to communicate with a said first or second reader, a memory to store said unique code and a power source to power said transponder all incorporated within said article, said transponder being triggered in response to receipt of an electromagnetic field applied thereto and transmitting the unique code by said wireless communicator to be read by said first or second reader.

Preferably, said first or second reader also comprises a wireless communicator, a store and an electromagnetic field generator, said electromagnetic field generator permeating a region adjacent to said first or second reader with an electromagnetic field and said wireless communicator of both said transponder of an article within said region and said first or second reader communicating with each other, so that said first or second reader may receive the unique code transmitted by said transponder, read and store the same in said store.

Preferably, the system includes a timer associated with said first or second reader or data logger to generate a real time and allow it to be stored at the instant when a said first or second reader reads a transmitted unique code.

Preferably, the system includes a temperature sensor associated with said second reader or data logger and said sanitiser, or alternatively with the article, to sense the sanitising temperature during a prescribed period when an article is disposed within said sanitiser.

Preferably, said second reader can store a plurality of unique codes or temperatures, and real times of reading thereof in said store thereof and download this data to said data logger at prescribed times.

Preferably, said first reader is associated with an alarm to trigger an alarm if an article is passed through a particular accessway.

Preferably, said second reader is associated with a reminder alarm to trigger a reminder alarm if an article is not sanitised at said prescribed interval(s).

Preferably, said reminder alarm triggers a reminder alarm if the sanitising temperature sensed during a prescribed period does not obtain a threshold maximum value.

Preferably, said sanitiser is a steriliser.

Preferably, the system includes a portable hand held device and a main data logger remote of said readers, the portable device using infrared transmission to transpose data collected from one or more said readers thereto at convenient times, and said portable device being adapted to download said collected data to said main data logger for subsequent storage and processing.

Preferably, said article is a knife.

Alternatively, said article may be a glove.

In accordance with another aspect of the present invention, there is provided a method for automatically logging a particular use of an article, comprising the steps of:

identifying a unique code associated with an article from the article;

automatically reading the identified unique code at a reading station in response to the article being passed adjacent a first reader at the reading station;

locating reading stations at one or more treatment or storage locations for the article within an area, with second readers disposed at each treatment or storage location for hygienically treating the article, and automatically reading the unique code of any article passing from or to said treatment or storage location;

sanitising said article at prescribed intervals at the treatment or storage location and logging the unique code and data associated with the hygienic treatment of said articles being sanitised.

Preferably, the method includes locating reading stations at one or more prescribed or controlled accessways to or from an area with readers disposed at each accessway, and automatically reading the unique code of any article passing through said accessway.

Preferably, the unique code is identified by applying an electromagnetic field to a region through which the article passes, and the article transmitting the unique code wirelessly in response to receipt of the electromagnetic field for reading by a first or second reader.

Preferably, the unique code is read by a first or second reader receiving the transmitted unique code, and storing the same in a store.

Preferably, the method includes storing the real time in the store at the time of reading the unique code.

Preferably, the method includes storing a plurality of unique codes of different articles together with the real times of reading the same and downloading this data to a remote main store at prescribed times to log the same.

Preferably, the method includes issuing an alarm if an article is passed through a particular accessway.

Preferably, the sanitising is a sterilisation process.

Preferably, the article is a knife.

Alternatively, the article is a glove.

In accordance with a further aspect of the invention, there is provided an article use monitoring system for hygiene purposes, comprising:

an identifier for incorporation within an article, the use of the article to be monitored and controlled, said identifier identifying a unique code for said article;

a reader of said identifier disposed at a treatment location for hygienically treating the article, said reader being adapted to automatically read said unique code in response to the article being passed adjacent said reader on entering or exiting the treatment location; and a data logger associated with said reader to log said unique code and data associated with the hygienic treatment of an article treated at the treatment location;

wherein one of said treatment locations includes a sanitiser for sanitising said article at prescribed intervals and said reader is prompted to read and log said unique code and said data associated with the hygienic treatment of articles whilst at said sanitiser.

Preferably, the system includes a timer associated with said reader or data logger to generate a real time and allow it to be stored at the instant when a said reader reads a unique code from said identifier of an article.

Preferably, the system includes a temperature sensor associated with said reader or data logger and said sanitiser to sense the sanitising temperature during a prescribed period when an article is disposed within said sanitiser.

Preferably, the reader can store a plurality of unique codes or temperatures, and real times of reading thereof in a store associated with said reader and download this data to said data logger at prescribed times.

Preferably, the reader is associated with a reminder alarm to trigger a reminder alarm if an article is not sanitised at said prescribed interval(s).

Preferably, said reminder alarm triggers a reminder alarm if the sanitisation temperature sensed during a prescribed period does not obtain a threshold maximum level.

Preferably, the sanitiser is a steriliser.

Preferably, the article is a knife and the use of the article is in the meat, fish and food handling industry.

Preferably, a treatment location is disposed in an area of an abattoir where the knife is used for skinning and boning of carcasses passed through the area by a conveyor.

Preferably, the area of the abattoir includes a series of work stations provided along the conveyor line where knife handlers situate to successively skin and bone carcasses passed along the conveyor line, and a treatment location is disposed within or adjacent to one or more of said work stations for knives to be treated therein following use by the knife handlers and to be retrieved therefrom for subsequent use.

Preferably, the area of the abattoir includes one or more accessways thereto, each accessway having a reader associated therewith to read and log movement of a knife therethrough for monitoring by said data logger.

Preferably, a reader is associated with an alarm means to trigger an alarm if a knife with a said identifier is passed through a particular said accessway.

In accordance with a further aspect of the invention, there is provided an article use monitoring system for hygiene purposes, comprising:

means for incorporation within an article for identifying a unique code for said article, the use of the article to be monitored and controlled;

means for automatically reading said unique code in response to the article being passed adjacent thereby on entering or exiting a treatment location for hygienically treating the article; and means for logging said unique code and data associated with the hygienic treatment of an article treated at the treatment location;

wherein one of said treatment locations includes means for sanitising said article at prescribed intervals and prompting the unique code and said data associated with the hygienic treatment of articles to be read and logged.

In accordance with a further aspect of the invention, there is provided a system for automatically logging data pertaining to a particular use of an article, comprising:

an article having means for identifying a unique code for said article incorporated therein;

means for reading said unique code disposed at a reading station to automatically read said unique code in response to the article being passed adjacent thereby, located in an area where the article is to be used;

said area having one or more treatment or storage locations for the article;

means for logging said unique code and a time at which said unique code was read;

wherein the unique code is automatically read on any passage of a said article from or to a said treatment or storage location; and wherein one of said treatment or storage locations includes means for sanitising said article at prescribed intervals and prompting said unique code and said time to be read and logged in connection with articles being sanitised thereby.

BRIEF DESCRIPTION OF THE DRAWINGS

The invention will be better understood in the light of the following description of several specific embodiments thereof. The description is made with reference to the accompanying drawings, wherein:

FIG. 1 is a series of drawings showing the manner in which the transponder is attached to the tang of a knife, whereby:

FIG. 2 is a schematic diagram showing the arrangement of a reading station at a steriliser;

FIG. 3 is a plan view of a steriliser showing the arrangement of the antenna at the opening to the steriliser;

FIG. 4 is a side view of an accessway showing the arrangement of the antenna around the door of the accessway in accordance with the first embodiment;

FIG. 5 is a schematic diagram showing the arrangement of the system in an area of an abattoir in accordance with the first embodiment.

BEST MODE(S) FOR CARRYING OUT THE INVENTION

Figure 1A:
FIG. 1A is a side view of the knife blade with the transponder affixed to the tang.

The first embodiment is directed to a system for automatically logging the use of an article in the form of a knife in an area of an abattoir where the knife is used for skinning and boning of carcasses passed through the area by means of a conveyor.

A plan view of the area 11 is shown in FIG. 5 of the drawings. The area essentially comprises a main working room 13, of generally rectangular shape, having a conveyor line 15 for transporting carcasses 17 of an animal to be processed, therethrough, adjacent one side wall 13a of the room.

A series of workstations 19 are provided along the conveyor line where knife handlers situate to successively skin and bone carcasses passed along the conveyor line 15.

An article treatment and storage location comprising a sanitising means in the form of a steriliser 21 is provided at each work station 19, which is operated by a number of knife handlers working at the work station to deposit used knives therein for cleaning and sterilising, and to retrieve treated knives therefrom for subsequent use. Moreover, each knife handler may have a plurality of knives which are used successively for working with successive carcasses, where a new knife is used after a prescribed time period, such as an hour or 20 minutes, or after a prescribed number of animals are worked on. The clean knives are stored in a hanger 23 at the work station 19 for successive use by the knife handler, and the used knives are successively placed by the knife handler into the steriliser 21, until there is a sufficient number to clean and sterilise in a single cleaning operation performed by the steriliser.

The room 13 has a number of prescribed or controlled accessways 25 thereto. Two main doors 25a and 25b are provided at opposite ends 13b and 13c of the room 13 to allow entry and exit into the work area of the room. A third door 25c, is provided along the other side wall 13d, which leads to a toilet and wash area 27.

A control room 29 is located remotely of the area 1, in which a main computer system 31 is located for centralising the storage of information and data pertaining to the use of all of the knives used in the area 11 and other similar areas within the abattoir.

A number of reading stations are located within the area, each having a reader 33 to read a code encoded upon or within, and uniquely identifying, each knife used in the area 11 and other areas of the abattoir, and timing means in the form of a real time clock to generate the real time and allow it to be stored at the instant when a unique code is read by the reader thereof. Some of the reading stations also have temperature sensing means provided to sense the maximum temperature of the environment surrounding the same during a prescribed time period between instances when the unique code is read by the reader.

Each reading station is connected into a data network 35 via a network card (not shown), and the data network is in turn similarly connected via a network card (not shown) to the main computer system 31. Accordingly, data acquired and accumulated by each reader 33 at each reading station is transmitted at prescribed times over the data network 35 to the main computer system 31 for data logging and storage in a main store or memory associated with the computer system.

The readers 33 are divided into two types, the first type 33a being associated with the knife treatment and storage locations, namely the sterilisers 21 and hangers 23, and the second type 33b being associated with prescribed or controlled accessways 25. The readers 33a associated with the sterilisers 21 and hangers 23 enable data to be logged in relation to the cleaning and use of the knives in the work areas 19, and the readers 33b associated with the accessways enable data to be logged in relation to the movement of knives into and out of the area 11. Both of these considerations are important to maintaining hygiene standards in the use of the knives within an abattoir environment.

Figure 1B:
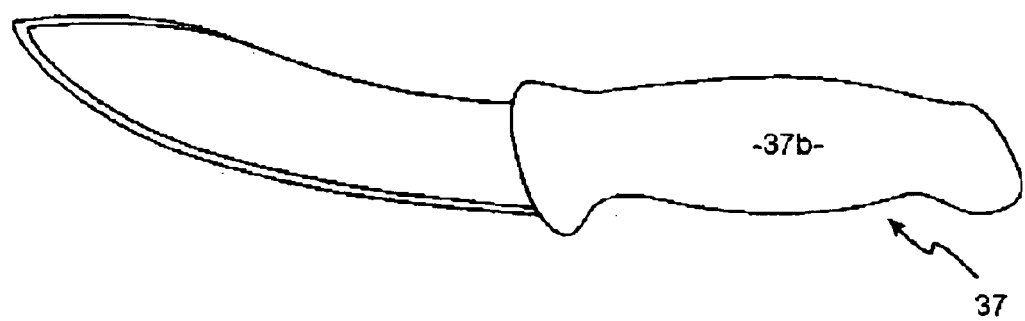
FIG. 1B is a side view of the knife with the handle affixed to the tang, encapsulating the transponder therein.
Figure 1C:
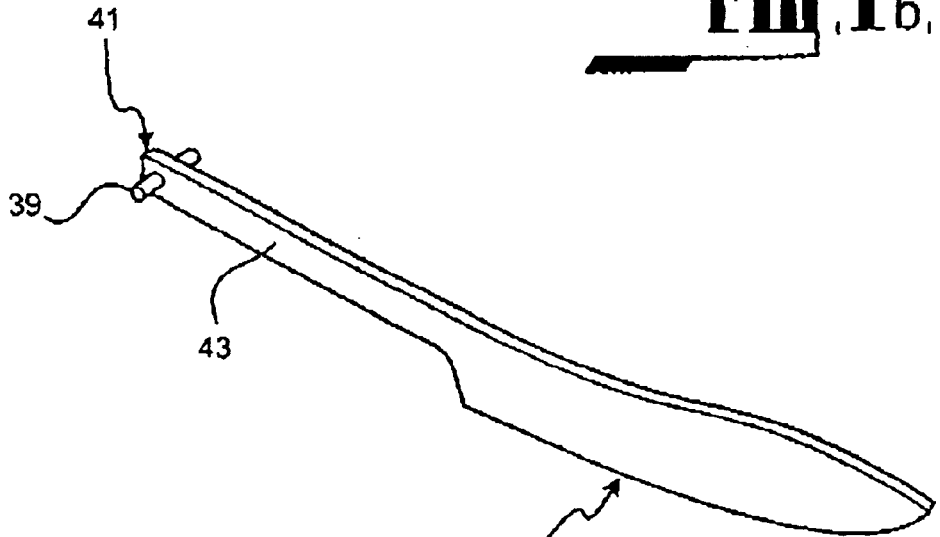
FIG. 1C is a perspective view of the knife blade showing the transponder affixed to the tang.

A knife 37 typically used for skinning carcasses in the abattoir is shown in FIG. 1 of the drawings.

As shown in the drawings the knife 37 includes an identifying means in the form of an encapsulated, cylindrical transponder means or transponder 39, which is affixed within an aperture 41 provided in the tang 43 of the knife blade 37a. The transponder 39 is disposed transversely of the knife tang 43 and projects out laterally and equidistantly from the tang so that it may be embedded centrally within the knife handle 37b.

Accordingly the knife handle 37b is moulded onto the tang 43 of the knife blade 37a and totally encapsulates the transponder 39 therein.

The transponder 39 includes wireless communication means to communicate with a reader 33 proximate thereto, memory means to store the code that uniquely identifies the knife 37 in the form of a digitally encoded number and powering means to power the transponder in response to receiving electromagnetic energy from an electromagnetic field applied to the transponder.

An appropriate form of transponder is the type known as Glass Tag (trade mark) by Sokymat Identification of Switzerland. This is a passive contactless transponder that communicates with the reader 33 via radio frequency transmission using the wireless communication means. The memory means of the transponder 39 is a read only memory storing the unique number code of the knife. The powering means includes an inductive coil, which induces a voltage therein to power the transponder when disposed in an electromagnetic field of sufficient strength. The induced AC voltage is rectified to provide an internal DC supply voltage. When the DC voltage exceeds the minimum level needed by the transponder to work properly, the transponder exchanges data, including the unique code, without physical contact to the reader 33.

The wireless communication means modulates and codes the data using Amplitude Shift Keying (ASK) with Manchester coding. The typical operating frequency used for the data transmission to the reader 33 is 125 kHz.

Each reader 33 comprises microcontroller means for communicating with the network card of the reading station thereof, wireless communication means to communicate with the wireless communication means of a transponder 39, storage means for storing identified unique codes of knives read by the reader, and an electromagnetic field generating means for generating an electromagnetic field to permeate a region 45 adjacent to the reader.

The microcontroller essentially controls the operation of the reader 33 in reading and storing data received by the wireless communication means, obtaining and storing the real time from the real time clock at the instant that data is read by the wireless communication means, and obtaining and storing the maximum temperature sensed by the temperature sensing means between prescribed instances of reading data on prescribed readers. The microcontroller also coordinates the transfer of accumulated data within the storage means with the network card, on transmitting the same over the data network 35 to the main computer system 31, when required to do so.

The wireless communication means includes a receiving antenna 47, which is powerful enough to receive a signal transmitted by the transponder 39 of a knife 37 disposed anywhere within the region 45.

The receiving antenna 47 is of a different type, depending on the particular type of reader. In the case of the readers 33a associated with the sterilisers 21, the antenna 47a is actually affixed around the neck of the steriliser, so as to cover the region 45a comprising the opening to the steriliser. In this manner, any knife 37 passing through the opening of the steriliser 21, either being placed in or being taken out of the steriliser, will have its unique code transmitted by the transponder 39 thereof, when passing through the region 45a, read by the reader 33a.

Similarly, in the case of the readers associated with the hangers 23, antennae (not shown) will be disposed immediately alongside the hanging position of each knife in the hanger 23, so that the region occupied by a knife handle 37b hung in the hanger will be covered. In this manner, any knife being placed in the hanger or being taken therefrom for use will have its unique code transmitted by the transponder thereof read by the reader 33a associated therewith.

In the case of the readers 33b associated with the accessways 25, the antenna 47b is actually affixed around the architrave of the door so as to cover the region 45b comprising the opening of the door. In this manner, any knife 37 passing through the opening of the door 25a, 25b,25c, either being taken into or from the room 13, will have its unique code transmitted by the transponder 39 thereof, when passing through the region 45b, read by the reader 33a.

The temperature sensing means comprises maximum temperature sensing transducers 49 which are associated with and incorporated into the design of each steriliser 21. As shown in FIG. 2 of the drawings, the transducer is located inside the steriliser to sense the temperature therein. The transducer is electronically connected to the reader 33a to operate in conjunction with the sensing of knives entering and exiting the steriliser 21 through the opening and allow a temperature reading to be logged during a prescribed time period. This time period corresponds to when a knife is in the steriliser 21 and the steriliser is operated. Accordingly, the reader 33a is provided with sufficient intelligence to determine when a knife is located in a steriliser by virtue of sensing its unique code as a result of it passing through the region 45a at the neck of the steriliser and sensing the temperature in the steriliser at a prescribed point in time during the sterilisation process. This temperature is recorded against each knife sensed to be disposed within the steriliser and is subsequently stored in storage means associated with the reader.

The storage means comprises any appropriate dynamic memory media that may have data written to, or read from it, by the microcontroller.

The electromagnetic field generating means includes a coil (not shown) that similarly surrounds the regions 45. Accordingly, the coil is pulsed continuously to generate an electromagnetic field that can induce sufficient voltage in the coil of any transponder 39 passing through the region 45 covered by the electromagnetic field, that can be rectified to exceed the minimum DC level required to activate the transponder data exchange.

In this manner, any knife 37 passing through a region 45 will be supplied with sufficient electromagnetic energy to power the transponder 39 thereof and transmit the unique code of the knife to be read by a reader.

The pulsing of the electromagnetic field and the frequency of the data exchange between the wireless communication means are designed to occur at a frequency offset that avoids interference with the data exchange. Moreover, the electromagnetic field is pulsed at power frequency levels, eg 50 Hz, whereas the data exchange is modulated in the radio frequency band.

The timing means of each reading station including a reader 33a associated with a steriliser 21 is also provided with a reminder alarm means (not shown) to trigger a reminder alarm (not shown) at prescribed time intervals. This time interval may simply be every hour or other fixed time period. Alternatively, it may be calculated on a more sophisticated basis by a computer program having regard to previously logged data concerning the knife. For example, the interval may be calculated from the time that a knife is logged as being taken out of a steriliser or a hanger 23 over a prescribed time period, which again may be one hour.

In operation, the readers 33 are operated continuously during a working period and accumulate data comprising the unique codes of knives and the times that they are passed through regions 45 sensed by the readers. Generally, there is sufficient memory capacity in a reader to accumulate data for an entire day. Accordingly, this data is downloaded to the main computer system 31 over the data network 35 at either the end of the day, or at periodical intervals throughout the day, if more frequent monitoring is required.

The data logged in the main computer 31 can be processed and statistical information concerning the use of each knife 37 used in the abattoir, can be obtained or derived. For example, the frequency of sterilising and the particular knives sterilised can be monitored and appropriate corrective action taken if a particular knife handler is not adhering to health regulations and standards.

The readers 33b associated with the accessways 25 can be used to connect to appropriate alarm means that may be activated when a knife is passed through an accessway so as to prevent removal or transfer of knives into regions of the abattoir where the further use or presence of the knife is strictly forbidden.

The second embodiment is substantially the same as the first embodiment except the data logging system is based on a much simpler and less sophisticated arrangement. Moreover, sterilising means in the form of the sterilisers 21 are not provided at each workstation, but instead a number of workstations share the one steriliser. In addition, reading stations and readers are not associated with each prescribed or controlled accessway and the data network is dispensed with entirely.

Instead, the sterilising means is a self contained, smart steriliser, which includes the entire reading station incorporating both the reader 33a and the timing means directly incorporated into its design.

Data concerning knife identification, as it passes through the opening of the steriliser and sterilisation temperature is collected by the reader 33a in the same manner as in the first embodiment. This data is transposed to, and collected by, a portable hand held device using infrared transmission from all of the smart sterilisers at convenient times. The portable device is then downloaded into the main computer 31.

In a further embodiment, the main computer is dispensed with and the readers themselves constitute the data logging means.

In another embodiment, the temperature sensing means is in the form of a temperature transducer incorporated into the knife handle itself, as opposed to the steriliser and is associated with the transponder to transmit the temperature of the environment surrounding the same at prescribed time periods corresponding to when the knife is undergoing a sterilisation process. Appropriate antennae and electromagnetic field generating means may be incorporated into the design of the steriliser at appropriate locations to enable the transponder to be activated at appropriate times during the sterilisation process.

In a further embodiment still, the sanitising means is a washing machine and the article is a safety glove. The cleaning and sanitising of gloves is another important consideration in meeting hygiene standards of abattoirs and food processing and the present invention lends itself perfectly to logging data pertaining to the use of gloves with knife handlers and monitoring the cleaning and sanitising thereof.

It should be apparent from the aforementioned embodiments that the identifying means of the knife and data logging can be put to useful effect in addition to sterilisation and movement tracking. For example, data logging of the use of a knife over a long period of time can create an entire history of the use of the knife, which can be used to make administrative decisions involving the further use of the knife. This history can also be feedback to the manufacturer of the knife to provide better quality control to aid in improving the design and manufacturing processes. In this respect, the transponder of each knife can include basic historical information concerning the knife, such as place and date of manufacture, and any other information that may be of use in identifying a knife or tracking its history. Correspondingly, the data logging of the use of the knife can be tailored to store appropriate data in relation to the date of purchase of the knife, the name of the person allocated the knife, changes in the name of the person allocated the knife, the number of grindings of the knife undertaken throughout its lifetime, etc. Accordingly, from this data predictions can be made as to the safe working life of the knife.

It should be appreciated that the scope of the present invention is not limited to the particular embodiment described herein. In particular, the invention in its broadest form need not be limited to the use of transponders of the type described in the preferred embodiment. In particular, other identifying means such as bar coding may be used to effect knife identification. Further still, the invention need not be limited to the data logging of knives and gloves, but may also have utility in the data logging of other articles, eg chain mesh, firearms, weapons, clothing or other articles need to be confined to an area or the use thereof within the area monitored. Accordingly, modifications to the embodiment may be envisioned to suit the particular article being logged and which do not depart from the spirit or scope of the present invention.

What is claimed is:

1. A system for automatically logging data pertaining to a particular use of an article, comprising:
   an article having identifier incorporated therein to identify a unique code for said article;
   a first reader of said identifier disposed at a reading station to automatically read said unique code in response to the article being passed adjacent said first reader;
   data logger associated with said first reader to log said unique code and a time at which said unique code was read by the first reader;
   said data logger being associated with one or more readers and reading stations located in an area where the article is to be used;
   said area having reading stations associated with one or more treatment or storage locations for the article; and
   a second reader being disposed at each treatment or storage location in a manner so that any passage of a said article from or to a said treatment or storage location requires the article to be passed adjacent said second reader at said reading station to enable said unique code in respect thereof to be automatically read by said second reader;
wherein one of said treatment or storage locations includes a sanitiser to sanitise said article at prescribed intervals and said second reader is prompted to read and log said unique code and said time in connection with articles passing to and from said sanitiser for sanitising thereof.

2. A system as claimed in claim 1, wherein said area has reading stations associated with one or more prescribed or controlled accessways thereto and therefrom, and a first reader is disposed at each accessway, such that any passage of a said article from or to the area will require the article to be passed adjacent a first reader at a said reading station so that said unique code in respect thereof will be automatically read by said first reader.

3. A system as claimed in claim 1, wherein the identifier comprises a transponder including a wireless communicator to communicate with a said first or second reader, a memory to store said unique code and a power source to power said transponder all incorporated within said article, said transponder being triggered in response to receipt of an electromagnetic field applied thereto and transmitting the unique code by said wireless communicator to be read by said first or second reader.

4. A system as claimed in claim 1, wherein said first or second reader also comprises a wireless communicator, store and an electromagnetic field generator, said electromagnetic field generator permeating a region adjacent to said first or second reader with an electromagnetic field and said wireless communicator of both said transponder of an article within said region and said first or second reader communicating with each other, so that said first or second reader may receive the unique code transmitted by said transponders, read and store the same in said store.

5. A system as claimed in claim 1, wherein the system includes timer associated with said first or second reader or data logger to generate a real time and allow it to be stored at the instant when a said first or second reader reads a transmitted unique code.

6. A system as claimed in claim 1, wherein the system includes a temperature sensor associated with said second reader or data logger and said sanitiser, or alternatively with the article, to sense the sanitising temperature during a prescribed period when an article is disposed within said sanitiser.

7. A system as claimed in claim 6, wherein said second reader can store a plurality of unique codes or temperatures, and real times of reading thereof in said store thereof and download this data to said data logger at prescribed times.

8. A system as claimed in claim 1, wherein said first reader is associated with an alarm to trigger an alarm if an article is passed through a particular accessway.

9. A system as claimed in claim 1, wherein said second reader is associated with a reminder alarm to trigger a reminder alarm if an article is not sanitised at said prescribed interval(s).

10. (Currently amended) A system as claimed in claim 9, wherein said reminder alarm triggers a reminder alarm if the sanitisation temperature sensed during a prescribed period does not obtain a threshold maximum level.

11. A system as claimed in claim 1, wherein said sanitiser is a steriliser.

12. A system as claimed in claim 1, wherein said article is a knife.

13. A system as claimed in claim 1, wherein said article is a glove.

14. A system as claimed in claim 1, including a portable hand held device and a main data logger remote of said first or second readers, the portable device using infrared transmission to transpose data collected from one or more said first or second readers thereto at convenient times, and said portable device being adapted to download said collected data to said main data logger for subsequent storage and processing.

15. A method for automatically logging a particular use of an article, comprising the steps of:
identifying a unique code associated with an article from the article;
automatically reading the identified unique code at a reading station in response to the article being passed adjacent a first reader at the reading station;
locating reading stations at one or more treatment or storage locations for the article within an area, with second readers disposed at each treatment or storage location for hygienically treating the article, and automatically reading the unique code of any article passing from or to said treatment or storage location;
sanitising said article at prescribed intervals at the treatment or storage location and logging the unique code and data associated with the hygienic treatment of said articles being sanitised.

16. A method as claimed in claim 15 including locating reading stations at one or more prescribed or controlled accessways to or from an area with first readers disposed at each accessway, and automatically reading the unique code of any article passing through said accessway.

17. A method as claimed in claim 15, wherein the unique code is identified by applying an electromagnetic field to a region through which the article passes, and the article transmitting the unique code wirelessly in response to receipt of the electromagnetic field for reading by a first or second reader.

18. A method as claimed in claim 15, wherein the unique code is read by a first or second reader receiving the transmitted unique code, and storing the same in a storage means.

19. A method as claimed in claim 15, including storing the real time in the storage means at the time of reading the unique code.

20. A method as claimed in claim 15, including storing a plurality of unique codes of different articles together with the real times of reading the same and downloading this data to a remote main store at prescribed times to log the same.

21. A method as claimed in claim 15, including issuing an alarm if an article is passed through a particular accessway.

22. A method as claimed in claim 15, wherein the sanitising is a sterilisation process.

23. A method as claimed in claim 15, wherein the article is a knife.

24. A method as claimed in claim 15, wherein the article is a glove.

25. An article use monitoring system for hygiene purposes, comprising:
an identifier for incorporation within an article, the use of the article to be monitored and controlled, said identifier identifying a unique code for said article;
a reader of said identifier disposed at a treatment location for hygienically treating the article, said reader being adapted to automatically read said unique code in response to the article being passed adjacent said reader on entering or exiting the treatment location; and a data logger associated with said reader to log said unique code and data associated with the hygienic treatment of an article treated at the treatment location;

wherein one of said treatment locations includes a sanitiser for sanitising said article at prescribed intervals and said reader is prompted to read and log said unique code and said data associated with the hygienic treatment of articles whilst at said sanitiser.

26. A system as claimed in claim 25, including a timer associated with said reader or data logger to generate a real time and allow it to be stored at the instant when a said reader reads a unique code from said identifier of an article.

27. A system as claimed in 25, including a temperature sensor associated with said reader or data logger and said sanitiser, or alternatively with an article, to sense the sanitising temperature during a prescribed period when an article is disposed within said sanitiser.

28. A system as claimed in claim 27, wherein said reader can store a plurality of unique codes or temperatures, and real times of reading thereof in a store associated with said reader and download this data to said data logger at prescribed times.

29. A system as claimed in claim 25, wherein said reader is associated with a reminder alarm to trigger a reminder alarm if an article is not sanitised at said prescribed interval(s).

30. A system as claimed in claim 29, wherein said reminder alarm triggers a reminder alarm if the sanitisation temperature sensed during a prescribed period does not obtain a threshold maximum level.

31. A system as claimed in claim 25, wherein said sanitiser is a steriliser.

32. A system as claimed in claim 25, wherein the article is a knife and the use of the article is in the meat, fish and food handling industry.

33. A system as claimed in claim 32, wherein a treatment location is disposed in an area of an abattoir where the knife is used for skinning and boning of carcasses passed through the area by a conveyor.

34. A system as claimed in claim 33, wherein said area of the abattoir includes a series of work stations provided along the conveyor line where knife handlers situate to successively skin and bone carcasses passed along the conveyor line, and a treatment location is disposed within or adjacent to one or more of said work stations for knives to be treated therein following use by the knife handlers and to be retrieved therefrom for subsequent use.

35. A system as claimed in claim 33, wherein said area of the abattoir includes one or more accessways thereto, each accessway having a reader associated therewith to read and log movement of a knife therethrough for monitoring by said data logger.

36. A system as claimed in claim 35, wherein a said reader is associated with an alarm to trigger an alarm if a knife with a said identifier is passed through a particular said accessway.

37. An article use monitoring system for hygiene purposes, comprising:

means for incorporation within an article for identifying a unique code for said article, the use of the article to be monitored and controlled;

means for automatically reading said unique code in response to the article being passed adjacent thereby on entering or exiting a treatment location for hygienically treating the article; and means for logging said unique code and data associated with the hygienic treatment of an article treated at the treatment location;

wherein one of said treatment locations includes means for sanitising said article at prescribed intervals and prompting the unique code and said data associated with the hygienic treatment of articles to be read and logged.

38. A system for automatically logging data pertaining to a particular use of an article, comprising:

an article having means for identifying a unique code for said article incorporated therein;

means for reading said unique code disposed at a reading station to automatically read said unique code in response to the article being passed adjacent thereby, located in an area where the article is to be used;

said area having one or more treatment or storage locations for the article;

means for logging said unique code and the time at which said unique code was read;

wherein the unique code is automatically read on any passage of a said article from or to a said treatment or storage location; and wherein one of said treatment or storage locations includes means for sanitising said article at prescribed intervals and prompting said unique code and said time to be read and logged in connection with articles being sanitised thereby.

* * * * *

UNITED STATES PATENT AND TRADEMARK OFFICE
CERTIFICATE OF CORRECTION

PATENT NO. : 6,867,698 B2
DATED : March 15, 2005
INVENTOR(S) : Herbert et al.

It is certified that error appears in the above-identified patent and that said Letters Patent is hereby corrected as shown below:

<u>Column 6,</u>
Line 35, replace "area 1," with -- area 11, --.

<u>Column 11,</u>
Line 29, replace "communicator, store" with -- communicator, a store --.
Line 37, replace "transponders" with -- transponder --.
Line 39, replace "includes timer" with -- includes a timer --.
Line 60, remove "(Currently amended)".

Signed and Sealed this

Eleventh Day of April, 2006

JON W. DUDAS
*Director of the United States Patent and Trademark Office*